United States Patent
Shevy

(10) Patent No.: US 7,180,657 B1
(45) Date of Patent: Feb. 20, 2007

(54) DEVICES USING HIGH PRECISION IN-FIBER ATOMIC FREQUENCY REFERENCE

(75) Inventor: Yaakov Shevy, Altadena, CA (US)

(73) Assignee: Orbits Lightwave, Inc., Pasadena, CA (US)

( * ) Notice: Subject to any disclaimer, the term of this patent is extended or adjusted under 35 U.S.C. 154(b) by 0 days.

(21) Appl. No.: 11/378,406

(22) Filed: Mar. 17, 2006

Related U.S. Application Data

(60) Provisional application No. 60/663,050, filed on Mar. 17, 2005.

(51) Int. Cl.
*H01S 3/00* (2006.01)
*H01S 3/13* (2006.01)
*G02B 6/02* (2006.01)

(52) U.S. Cl. .................. 359/342; 372/32; 385/125
(58) Field of Classification Search ............... 354/342; 372/32; 385/125
See application file for complete search history.

(56) References Cited

U.S. PATENT DOCUMENTS

| | | | |
|---|---|---|---|
| 6,496,634 B1 * | 12/2002 | Levenson | 385/125 |
| 6,768,750 B2 * | 7/2004 | Kuksenkov | 372/20 |
| 2005/0018987 A1 | 1/2005 | Ruf et al. | 385/125 |

OTHER PUBLICATIONS

Shevy and Deng, "Frequency stable and ultranarrow-linewidth semiconductor laser locked directly to an atomic-cesium transition," Optics Letters, vol. 23, No. 6, pp. 472-474 (Mar. 15, 1998).
Shevy, Kitching and Yariv, "Linewidth reduction and frequency stabilization of a semiconductor laser with a combination of FM sideband locking and optical feedback," Optics Letters, vol. 18, No. 13, pp. 1071-1073 (Jul. 1, 1993).

* cited by examiner

*Primary Examiner*—Mark Hellner
(74) *Attorney, Agent, or Firm*—Fish & Richardson P.C.

(57) ABSTRACT

Techniques and devices based on holey fibers with internal holes that confine a gas medium for various applications.

9 Claims, 3 Drawing Sheets

Fiber Cross Section

DEVICES USING HIGH PRECISION IN-FIBER ATOMIC FREQUENCY REFERENCE

This application claims the priority of U.S. Provisional Application No. 60/663,050 entitled "HIGH PRECISION IN-FIBER ATOMIC FREQUENCY REFERENCE" and filed on Mar. 17, 2005, the entire disclosure of which is incorporated herein by reference as part of this application.

BACKGROUND

This application relates to optical frequency reference and applications use such a reference.

Atomic or molecular transitions in various atomic or molecular media may be used to provide precision frequency references in a variety of applications. For example, many precision laser applications require frequency stability on both short and long time scales, and sometimes even absolute frequency calibration. Atomic and molecular gases are commonly used to produce frequency references for stabilizing lasers and locking laser frequencies. Frequency locking in a laser can be achieved by reference to an atomic absorption line in an atomic or molecular gas. Bulky glass absorption cells and free space optics are typically used in such frequency locking systems.

SUMMARY

This application describes devices and techniques that use a fiber with internal holes that confine a gas medium. In one implementations, a fiber device includes a fiber having internal holes; a gas medium filled in at least one of the internal holes and exhibiting an atomic or molecular transition to provide an optical frequency reference; a first fiber grating formed in the fiber; and a second fiber grating formed in the fiber, wherein the first and second fiber gratings are spaced to include the gas medium therebetween.

In another implementation, a fiber device includes a fiber having internal holes; a gas medium filled in at least one of the internal holes and exhibiting an atomic transition to provide an optical frequency reference; and two chirped fiber gratings with a spatial offset formed in the fiber to effectuate an in-fiber comb filter.

In another implementation, a fiber device includes a holey fiber segment comprising internal holes at least one of which is filled with a gas medium exhibiting an atomic or molecular transition to provide an optical frequency reference; and a fiber module operable to split a laser beam into a pump laser beam and a probe laser beam and coupled to the fiber segment to supply the pump laser beam to the holey fiber segment and the probe laser beam to the holey fiber segment in an opposite direction to the pump laser beam.

In addition, a device is described to include a laser to produce a laser beam; and a laser control module that receives at least a portion of the laser beam and to feed a feedback light beam generated from the received portion to the laser to stabilize the laser. The laser control module includes a frequency reference cell which comprises a fiber having internal holes and a gas medium filled in at least one of the internal holes to exhibit an atomic transition to provide an optical frequency reference at which the laser is stabilized.

This application also describes a method using a holey fiber to perform saturation absorption measurements. A pump beam is coupled into a holey fiber filled with an atomic or molecular gas in holes within the holey fiber with or without the fiber gratings. A probe beam is also coupled into the holey fiber in an opposite direction of the pump beam. The transmission of the probe beam is then directed through the holey fiber to obtain a Doppler-free saturation spectroscopy spectrum of the gas in the holey fiber. Such a spectrum can provide ultra-narrow spectral features that can be used as precision frequency references for various applications.

These and other implementations and their operations and other features are described in greater detail in the attached drawings, the detailed description and the claims.

DETAILED DESCRIPTION

Figure 1:
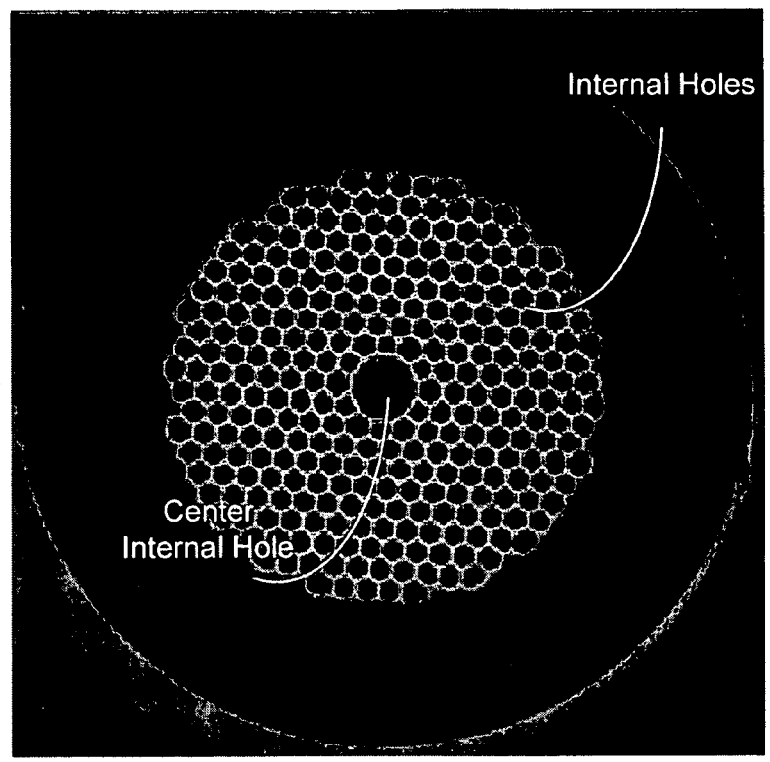
FIG. 1 shows a photograph of a holey fiber made by Blaze photonics.

Optical frequency reference based on bulky glass absorption cells and free space optics are not practical in various applications. For optical frequencies used for the optical communications, Acetylene ($C_2H_4$) Hydrogen Cyanide (HCN) and their isotopes possess a manifold of lines and can be used as frequency references to calibrate lasers, e.g., the lasers used in DWDM communication bands around 1550 nm. However, glass absorption cells containing Acetylene ($C_2H_4$) Hydrogen Cyanide (HCN) gases usually require optical alignment in free space from the cells to fiber pigtails. Such alignment is difficult to achieve and is sensitive to vibrations and other effects. Moreover, the molecular absorption lines are Doppler broadened and such broadening can lead to absorption line-shapes with linewidths in the order of 10 GHz FWHM. Such wide linewidths are too broad for many applications that require better frequency precision at much narrow linewidths, e.g. at MHz or sub-MHz range for the frequency precision or frequency stability.

The Doppler broadening may be mitigated via various techniques. For example, a Doppler-free atomic spectrum may be extracted by using saturation spectroscopy techniques which may be implemented by measuring the intensity of a weak probe laser field counter-propagating to a strong laser pump which saturates the transition. Due to the simultaneous interaction of the atomic transition with the spatially overlapped probe beam and pump beam, the probe exhibits a maximum transmission within the Doppler-broadened line when the probe and pump interact with stationary or near stationary atoms in the overlapped region and hence a Doppler free atomic reference line can be observed.

The above Doppler-free saturation spectroscopy, however, can be difficult to implement with gaseous media due to various technical issues. As one example, various molecular or atomic spectral lines may have a small dipole moment and therefore the associated optical absorption is relatively week. Hence, in order to obtain a sufficient amount of absorption, the cell length need be sufficiently long. As another example, the atoms or molecules in a gas cell collide with each other and thus exhibits collisional broadening of the transition linewidth, e.g., 30 MHz/torr for HCN. This collisional line broadening increases the actual optical saturation intensity of the transition, e.g., at or greater than about 2000 W/cm$^2$. Such high saturation intensities may be difficult to achieve with single-frequency lasers due to cost and technical limitations. For a usual gas cell with a pump power at the mW level and a beam size of about 1 mm, a few parts per million saturation-spectroscopy signal may be observed. The signal to noise ratio of the signal may be too low to be practical for many applications.

This application describes techniques and devices based on in-fiber atomic or molecular frequency references. A holey fiber is used to confine an atomic or molecular medium to replace the conventional vapor cell and the associated free-space optics for directing the probe and pump beams. Holey fibers guide light using the microstructure of the fiber rather than the refractive index profile. In some holey fibers, most of the light propagates in a hollow-core structure.

FIG. 1 illustrates one example of a holey fiber that has a center internal hole and peripheral internal holes along the longitudinal direction of the fiber. These holes form a period structure which creates band gaps for confined light in the fiber. The center internal hole at the fiber core can be filled with an atomic or molecular gas to induce a sufficient amount of the gas-light interaction within the fiber. Under this design, it is possible to achieve a long interaction length with a nearly perfect optical alignment between the counter-propagating pump and probe beams. A long holey fiber for a long interaction length can be arranged into a compact loop, e.g., a loop with a diameter of 5 cm. In addition, due to the small laser field mode diameter (e.g., in the order of 10 microns), the intensity of the laser beam inside the fiber even with a low power input beam (e.g., a 10-mW input laser beam) can be sufficiently high to satisfy the intensity requirement for the saturation absorption spectroscopy. In this example, the intensity is $I=(10^{-2} W)/\pi(10^{-3} cm)^2=3000$ W/cm$^2$. Hence, a holey fiber filled with an atomic gas in its holes can meet the requirements for saturation-spectroscopy: (i) a high laser intensity, (ii) a long interaction length and (iii) desired spatial overlap of the counter-propagating pump and probe beams. In practice, at least the center internal hole is filled with a desired gas medium in some implementations. In other implementations, the center and at least some of the peripheral internal holes can be filled with the gas medium. The two ends of each gas-filled hole are sealed to confine the gas.

One exemplary application of this in-fiber atomic reference is to achieve Doppler-free atomic spectra in an all fiber device with low power laser beams. In implementation, a few loops of a holey fiber cell (e.g., on the order of one meter) filled with a low pressure reference gas is used to receive counter propagating laser probe and pump beams to obtain a saturation spectroscopy locking signal. This signal can be obtained by means of FM sidebands spectroscopy that can yield a dispersive lineshape or by the use of the pump beam modulation and a lock-in amplifier. In another implementation, an in-fiber Bragg grating cavity may be formed in the holey fiber to enhance the effective interaction length and the laser intensity. In yet another implementation, an in-fiber comb filter may be used to translate the atomic reference line.

Figure 2:
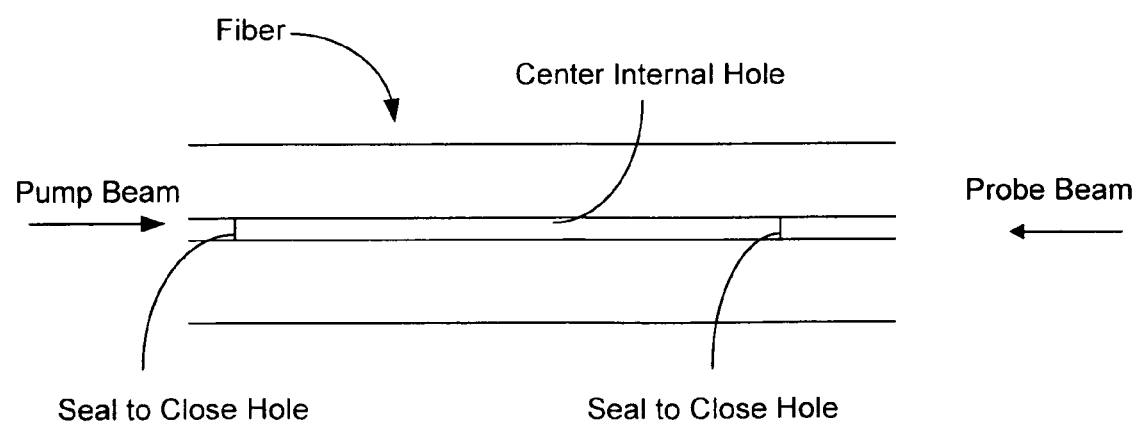
FIG. 2 shows an example of a saturation absorption spectroscopy device in a gas filled holey fiber based on one implementation.

FIG. 2 illustrates an example of a sealed gas filled holey fiber and counter-propagating laser beams to obtain saturation spectroscopy signal. The error signal from saturation spectroscopy can be obtained by FM sidebands locking. See Shevy and Deng, "Frequency stable and ultranarrow-linewidth semiconductor laser locked directly to an atomic-cesium transition," Optics Letters, Volume 23, No. 6, pp. 472–474 (Mar. 15, 1998); and Shevy, Kitching and Yariv, "Linewidth reduction and frequency stabilization of a semiconductor laser with a combination of FM sideband locking and optical feedback," Optics Letters, Volume 18, No. 13, pp. 1071–1073 (Jul. 1, 1993), which are incorporated by as part of the specification of this application. Alternatively, the error signal from saturation spectroscopy can be obtained by modulating the pump intensity and using a lock-in amplifier in detecting the probe transmission.

Figure 3:
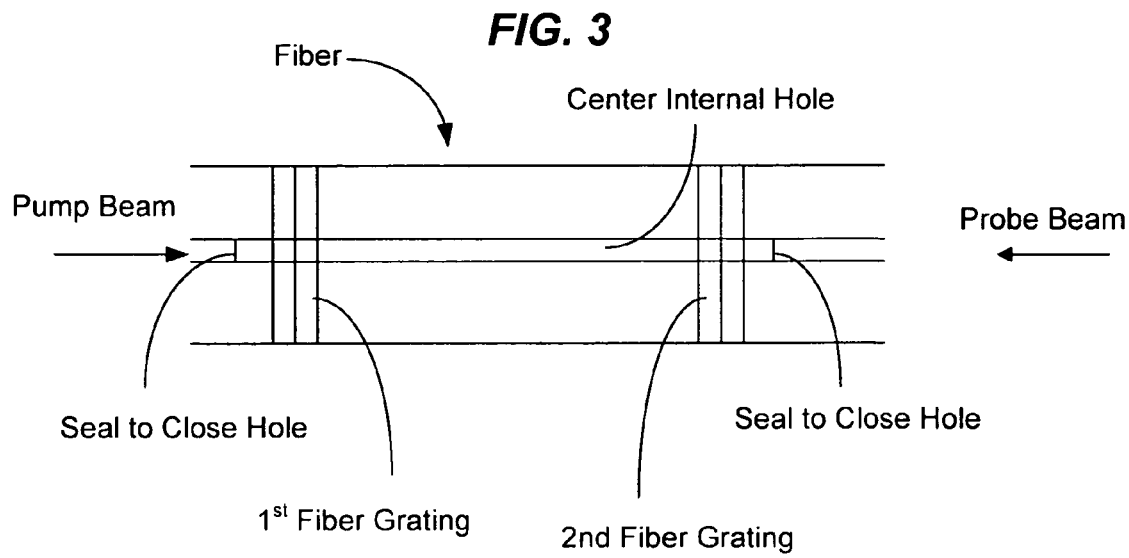
FIG. 3 shows an example a saturation absorption spectroscopy in a gas filled holey fiber enhanced with an optical cavity formed by in in-fiber Bragg mirrors.

FIG. 3 shows a gas-filled holey fiber with a built-in resonant cavity operating with two counter-propagating beams. Such an optical cavity can be formed by imprinting Bragg gratings in the fiber by, e.g., using UV light to modify the index of the UV-sensitive portion of the holey fiber. The resonant cavity enhances the laser intensity and increases the effective length of the interaction. Such a filter can enhance the laser intensity by many folds and the effective length due to the filter delay can be increased by, e.g., at least a factor of ten. A more complicated Bragg grating can be used, e.g., using two or more sets of fiber gratings such as a three-grating structure to obtain a flat top resonant transmission feature. If the flat-top resonant transmission band is spectrally aligned with a Doppler broadened atomic line, the laser frequency can be tuned without changing the laser intensity. Also the flat top filter can be designed to provide an even longer delay and therefore a longer interaction length.

Figure 4:
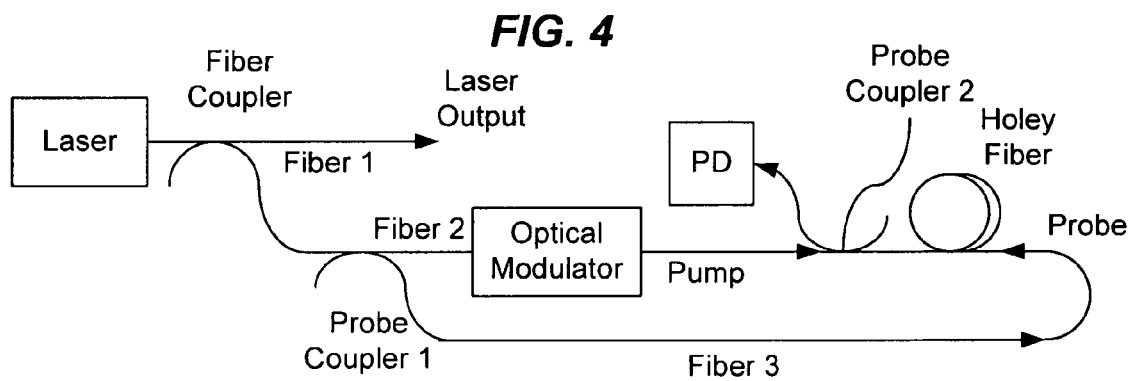
FIG. 4 shows a device that implements a gas filled holey fiber shown in FIG. 2 or 3 and a fiber system that provides counter-propagating beams using a common laser.

FIG. 4 shows a device that implements a gas filled holey fiber shown in FIG. 2 or 3 and a fiber system that provides counter-propagating beams using a common laser. A laser such as a semiconductor laser is coupled to a fiber 1 which receives and guides the laser light from the laser. A fiber coupler is coupled to the fiber 1 to split a portion of the laser light into a fiber 2 while the remaining light in the fiber 1 is used as the output for the device. A probe fiber coupler 1 is coupled to the fiber 2 to further split the laser light in fiber 2 into a pump beam in the fiber 2 and a probe beam in a third fiber 3. A holey fiber segment is connected between the other two ends of the fibers 2 and 3 so that the pump and probe beams are directed to counter propagate in the holey fiber segment for the saturation absorption measurement. An optical modulator may be coupled in the fiber 2 between the probe coupler 1 and the holey fiber segment to modulate the intensity of the pump. A second probe coupler 2 is coupled in the fiber 2 to couple the probe beam that transmits through the holey fiber to a photodetector (PD) for the saturation absorption measurement. An optical isolator may be coupled in each of the fiber 2 and fiber 3 to prevent optical feedback to the laser.

Figure 5:
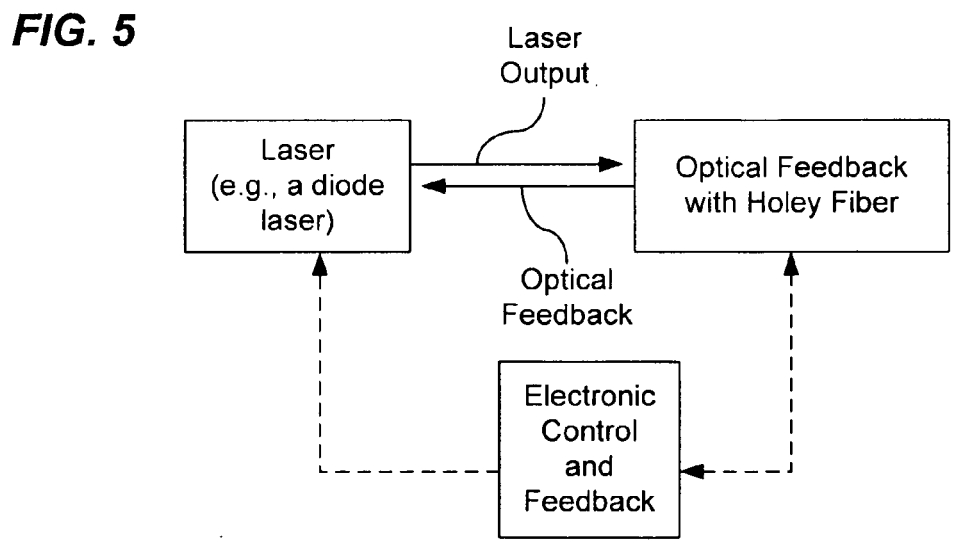
FIG. 5 shows an example of an in-fiber frequency comb filter with a frequency spacing of 12.5 GHz with a low loss and good channel uniformity where the chart in the middle shows a frequency deviation less than 1 GHz and the chart at the bottom shows a relatively uniform linewidth at different wavelengths from 1557 nm to 1563 nm.

One limitation of using atomic-resonances is that atomic or molecular resonances are available only at limited frequencies dictated by the natural atomic or molecular structure of a gas. This limitation may be removed by using an in-fiber frequency ruler, i.e., an in-fiber comb filter to translate the atomic resonance frequency to a different frequency. FIG. 5 shows such a comb filter structure in a holey fiber obtained by imprinting two chirped Bragg grating with a spatial offset. The atomic and molecular line of the sealed gas in the holey fiber and the comb filter can be used in combination to improve the frequency stability because of the absolute frequency stability of the atomic transition where the separation between the comb filter peaks remains constant.

Figure 6:
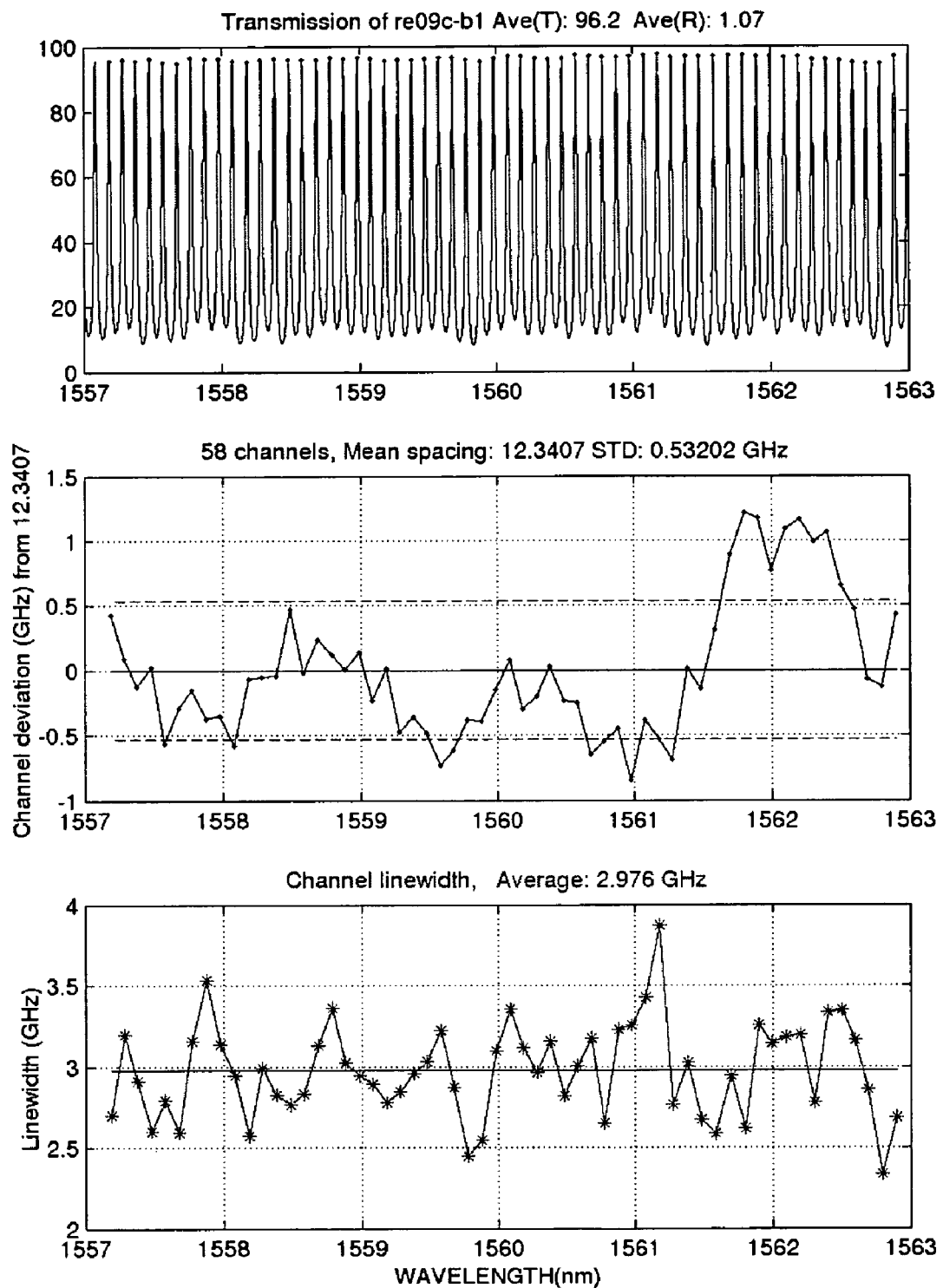
FIG. 6 shows a laser stabilization system using an optical feedback with a holey fiber.

The in-fiber atomic reference cell described may be used to replace a glass vapor glass cell in various applications such as laser stabilization systems where the optical transmission through the vapor cell at a selected transition is fed back to the laser to stabilize the laser. FIG. 6 shows a laser stabilization system using an optical feedback with a holey fiber and an electronic control and feedback unit. The laser to be stabilized can be in various configurations, including a fiber laser in a fiber which may be separate from the holey fiber or may be part of the holey fiber where the atomic cell resides, a diode laser, a solid-state laser, and others. Techniques using FM sideband modulation for stabilizing diode lasers are described in two articles incorporated herein by references and can be implemented with the in-fiber atomic reference cell.

Only a few implementations are disclosed. However, it is understood that variations and enhancements may be made.

What is claimed is:

1. A device, comprising:
   a laser to produce a laser beam; and
   a laser control module that receives at least a portion of the laser beam and to feed a feedback light beam generated from the received portion to the laser to stabilize the laser, wherein the laser control module comprises a frequency reference cell which comprises a fiber having internal holes and a gas medium filled in at least one of the internal holes to exhibit an atomic transition to provide an optical frequency reference at which the laser is stabilized.

2. The device as in claim 1, wherein the laser is a diode laser.

3. The device as in claim 1, wherein the laser is a fiber laser.

4. The device as in claim 1, wherein the laser is a solid-state laser.

5. The device as in claim 2, wherein the diode laser is modulated by a frequency modulation control to produce frequency modulation sidebands.

6. A device, comprising:
   a holey fiber segment comprising internal holes at least one of which is filled with a gas medium exhibiting an atomic or molecular transition to provide an optical frequency reference; and
   a fiber module operable to split a laser beam into a pump laser beam and a probe laser beam and coupled to the fiber segment to supply the pump laser beam to the holey fiber segment and the probe laser beam to the holey fiber segment in an opposite direction to the pump laser beam.

7. The device as in claim 6, wherein the fiber module comprises:
   a first fiber operable to receive the laser beam and is connected to a first end of the holey fiber segment;
   a first fiber coupler coupled to the first fiber to split a first portion of the laser beam as the probe laser beam while the remaining light in the first fiber as directed to the holey fiber segment as the pump laser beam; and
   a second fiber having a first end coupled to the first fiber coupler to receive the probe laser beam and a second end coupled to a second end of the holey fiber segment to direct the probe laser beam into the holey fiber segment.

8. The device as in claim 6, further comprising:
   a first fiber grating formed in the holey fiber segment; and
   a second fiber grating formed in the holey fiber segment, wherein the first and second fiber gratings are spaced to include the gas medium therebetween.

9. The device as in claim 6, further comprising two chirped fiber gratings with a spatial offset formed in the holey fiber segment to effectuate an in-fiber comb filter.

* * * * *